(12) United States Patent
Gesing et al.

(10) Patent No.: US 6,451,738 B1
(45) Date of Patent: Sep. 17, 2002

(54) SUBSTITUTED THIENYL(AMINO)-SULPHONYL(THIO)UREAS AS HERBICIDES

(75) Inventors: Ernst Rudolf F. Gesing, Erkrath; Johannes Rudolf Jansen, Monheim; Klaus-Helmut Müller, Düsseldorf; Ulrich Philipp, Köln, all of (DE); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/925,801

(22) Filed: Aug. 9, 2001

Related U.S. Application Data

(62) Division of application No. 09/319,411, filed as application No. PCT/EP97/06617 on Nov. 27, 1997, now Pat. No. 6,303,541.

(30) Foreign Application Priority Data

Dec. 9, 1996 (DE) .......................................... 196 51 037

(51) Int. Cl.⁷ ........................ C07D 409/12; A01N 43/54
(52) U.S. Cl. ........................ 504/215; 544/300; 544/310; 544/318; 544/320; 544/324
(58) Field of Search .......................... 504/215; 544/300, 544/310, 318, 320, 324

(56) References Cited

U.S. PATENT DOCUMENTS 4,169,719 A * 10/1979 Levitt .......................... 504/215
4,398,939 A * 8/1983 Levitt .......................... 504/215

\* cited by examiner

*Primary Examiner*—John M. Ford
(74) *Attorney, Agent, or Firm*—Joseph C. Gil

(57) ABSTRACT

The invention relates to novel substituted thienyl(amino)sulphonyl(thio)ureas of the formula (I)

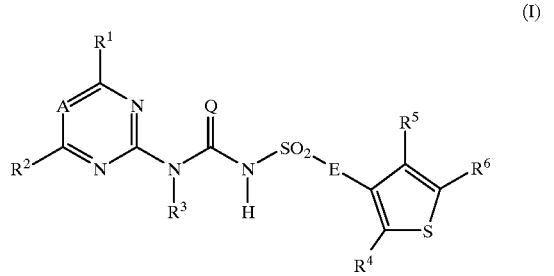

(I)

in which

A represents nitrogen or a CH grouping,

E represents a single bond or an NH grouping,

Q represents oxygen or sulphur, $R^1$ and $R^2$ independently of one another represent hydrogen, halogen or in each case optionally substituted alkyl, alkoxy, alkylthio, alkylamino, dialkylamino, cycloalkyl, cycloalkyloxy, aryloxy or heterocyclyloxy, $R^3$ represents hydrogen or optionally substituted alkyl, $R^4$ and $R^5$ independently of one another each represent cyano, halogen or represent in each case optionally substituted alkyl, alkoxy, alkenyl, alkenyloxy, alkinyl or alkinyloxy, and $R^6$ represents hydrogen, cyano, halogen or represents in each case optionally substituted alkyl, alkoxy, alkenyl, alkenyloxy, alkinyl or alkinyloxy, and to salts of compounds of the formula (I), to processes for preparing the novel compounds and to their use as herbicides.

10 Claims, No Drawings

SUBSTITUTED THIENYL(AMINO)-SULPHONYL(THIO)UREAS AS HERBICIDES

This a Divisional Application of Ser. No. 09/319,411, filed Jun. 3, 1999, now U.S. Pat. No. 6,303,541, which is a 371 of application Ser. No. PCT/EP97/06617, filed Nov. 27, 1997.

The invention relates to novel substituted thienyl(amino)sulphonyl(thio)ureas, to processes for their preparation and to their use as herbicides.

BACKGROUND OF THE INVENTION

It is already known that certain substituted thienylsulphonylureas have herbicidal properties (cf. U.S. Pat. No. 4,127,405, U.S. Pat. No. 4,169,719, U.S. Pat. No. 4,398,939, U.S. Pat. No. 4,523,943). However, the herbicidal activity of these known compounds is not satisfactory in all aspects.

DETAILED DESCRIPTION OF THE INVENTION

This invention, accordingly, provides the novel substituted thienyl(amino)sulphonyl(thio)ureas of the general formula (I)

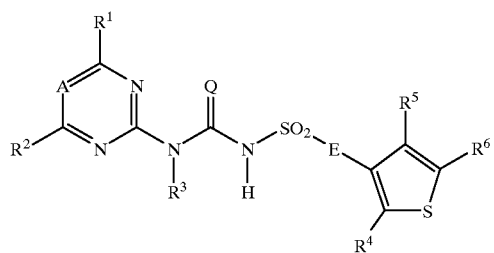

in which
- A represents nitrogen or a CH grouping,
- E represents a single bond or an NH grouping,
- Q represents oxygen or sulphur,
- $R^1$ represents hydrogen, halogen or in each case optionally substituted alkyl, alkoxy, alkylthio, alkylamino, dialkylamino, cycloalkyl, cycloalkyloxy, aryloxy or heterocyclyloxy,
- $R^2$ represents hydrogen, halogen or in each case optionally substituted alkyl, alkoxy, alkylthio, alkylamino, dialkylamino, cycloalkyl, cycloalkyloxy, aryloxy or heterocyclyloxy,
- $R^3$ represents hydrogen or optionally substituted alkyl,
- $R^4$ represents cyano, halogen or represents in each case optionally substituted alkyl, alkoxy, alkenyl, alkenyloxy, alkinyl or alkinyloxy,
- $R^5$ represents cyano, halogen or represents in each case optionally substituted alkyl, alkoxy, alkenyl, alkenyloxy, alkinyl or alkinyloxy, and
- $R^6$ represents hydrogen, cyano, halogen or represents in each case optionally substituted alkyl, alkoxy, alkenyl, alkenyloxy, alkinyl or alkinyloxy, and salts of compounds of the formula (I).

The novel substituted thienyl(amino)sulphonyl(thio)ureas of the general formula (I) are obtained when
in the case of E representing a single bond in the general formula (I)

(a) aminoazines of the general formula (II)

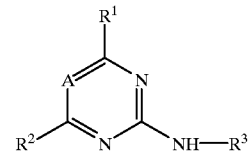

in which
- A, $R^1$, $R^2$ and $R^3$ are each as defined above, are reacted with thienylsulphonyl iso(thio)cyanates of the general formula (III)

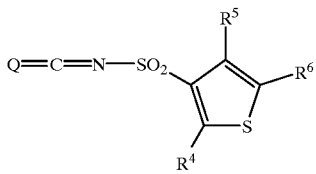

in which
- Q, $R^4$, $R^5$ and $R^6$ are each as defined above,
- if appropriate in the presence of a reaction auxiliary and if appropriate in the presence of a diluent, or (b) substituted aminoazines of the general formula (IV)

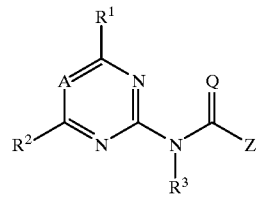

in which
- A, Q, $R^1$, $R^2$ and $R^3$ are each as defined above and
- Z represents halogen, alkoxy or aryloxy, are reacted with thiophenesulphonamides of the general formula (V)

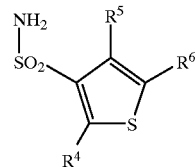

in which
- $R^4$, $R^5$ and $R^6$ are each as defined above,
- if appropriate in the presence of a reaction auxiliary and if appropriate in the presence of a diluent, or (c) aminoazines of the general formula (II)

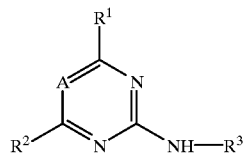
(II)

in which

A, $R^1$, $R^2$ and $R^3$ are each as defined above, are reacted with substituted thiophenesulphon(thio) amides of the general formula (VI)

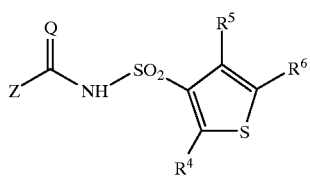
(VI)

in which

Q, $R^4$, $R^5$ and $R^6$ are each as defined above and

Z represents halogen, alkoxy or aryloxy, if appropriate in the presence of a reaction auxiliary and if appropriate in the presence of a diluent, or when—in the case that E represents an NH grouping (d) aminoazines of the general formula (II)

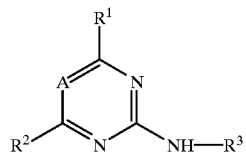
(II)

in which

A, $R^1$, $R^2$ and $R^3$ are each as defined above are reacted with chlorosulphonyl iso(thio)cyanate, if appropriate in the presence of a diluent, and the resulting chlorosulphonylureas of the general formula (VII)

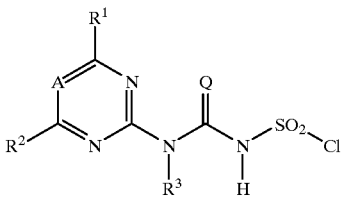
(VII)

in which

A, Q, $R^1$, $R^2$ and $R^3$ are each as defined above are reacted with aminothiophenes of the general formula (VIII)

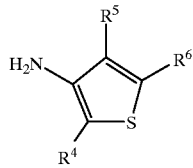
(VIII)

in which $R^4$, $R^5$ and $R^6$ are each as defined above, if appropriate in the presence of a reaction auxiliary and if appropriate in the presence of a diluent, and the compounds of the formula (I) obtained by processes (a), (b), (c) or (d) are optionally converted into salts by customary methods.

The novel substituted thienyl(amino)sulphonyl(thio)ureas of the general formula (I) have strong herbicidal activity.

The invention preferably provides compounds of the formula (I) in which

A represents nitrogen or a CH grouping,

E represents a single bond or an NH grouping,

Q represents oxygen or sulphur, $R^1$ represents hydrogen, halogen, represents in each case optionally cyano-, halogen- or $C_1$–$C_4$-alkoxy-substituted alkyl, alkoxy, alkylthio, alkylamino or dialkylamino having in each case 1 to 4 carbon atoms in the alkyl groups, represents in each case optionally cyano-, halogen-, $C_1$–$C_4$-alkyl- or $C_1$–$C_4$-alkoxy-substituted cycloalkyl or cycloalkyloxy having in each case 3 to 6 carbon atoms, or represents in each case optionally cyano-, halogen-, $C_1$–$C_4$-alkyl- or $C_1$–$C_4$-alkoxy-substituted phenoxy, oxetanyloxy, furyloxy or tetrahydrofuryloxy, $R^2$ represents hydrogen or halogen, represents in each case optionally cyano-, halogen- or $C_1$–$C_4$-alkoxy-substituted alkyl, alkoxy, alkylthio, alkylamino or dialkylamino having in each case 1 to 4 carbon atoms in the alkyl groups, represents in each case optionally cyano-, halogen-, $C_1$–$C_4$-alkyl- or $C_1$–$C_4$-alkoxy-substituted cycloalkyl or cycloalkyloxy having in each case 3 to 6 carbon atoms, or represents in each case optionally cyano-, halogen-, $C_1$–$C_4$-alkyl- or $C_1$–$C_4$-alkoxy-substituted phenoxy, oxetanyloxy, furyloxy or tetrahydrofuryloxy, $R^3$ represents hydrogen or optionally $C_1$–$C_4$-alkoxy-, $C_1$–$C_4$-alkyl-carbonyl- or $C_1$–$C_4$-alkoxy-carbonyl-substituted alkyl having 1 to 4 carbon atoms, $R^4$ represents cyano, halogen, represents optionally cyano-, halogen- or $C_1$–$C_4$-alkoxy-substituted $C_1$–$C_4$-alkyl, represents in each case optionally cyano- or halogen-substituted $C_2$–$C_4$-alkenyl or $C_2$–$C_4$-alkinyl, represents optionally cyano-, halogen- or $C_1$–$C_4$-alkoxy-substituted $C_1$–$C_4$-alkoxy, or represents in each case optionally cyano- or halogen-substituted $C_2$–$C_4$-alkenyloxy or $C_2$–$C_4$-alkinyloxy, $R^5$ represents cyano, halogen, represents optionally cyano-, halogen- or $C_1$–$C_4$-alkoxy-substituted $C_1$–$C_4$-alkyl, represents in each case optionally cyano- or halogen-substituted $C_2$–$C_4$-alkenyl or $C_2$–$C_4$-alkinyl, represents optionally cyano-, halogen- or $C_1$–$C_4$-alkoxy-substituted $C_1$–$C_4$-alkoxy, or represents in each case optionally cyano- or halogen-substituted $C_2$–$C_4$-alkenyloxy or $C_2$–$C_4$-alkinyloxy, and $R^6$ represents hydrogen, represents cyano, halogen, represents optionally cyano-, halogen- or $C_1$–$C_4$-alkoxy-substituted $C_1$–$C_4$-alkyl, represents in each case optionally cyano- or halogen-substituted $C_2$–$C_4$-alkenyl or $C_2$–$C_4$-alkinyl, represents optionally cyano-, halogen- or $C_1$–$C_4$-alkoxy-substituted $C_1$–$C_4$-alkoxy, or represents in each case optionally cyano- or halogen-substituted $C_2$–$C_4$-alkenyloxy or $C_2$–$C_4$-alkinyloxy.

The invention furthermore preferably provides sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which A, E, Q, $R^1$, $R^2$, $R^3$, $R^4$, $R^5$ and $R^6$ are each preferably as defined above.

The invention in particular provides compounds of the formula (I) in which

A represents nitrogen or a CH grouping,

E represents a single bond or an NH grouping,

Q represents oxygen or sulphur, $R^1$ represents hydrogen, fluorine, chlorine, bromine or in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethlylamino or diethylamino, $R^2$ represents fluorine, chlorine, bromine or in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^3$ represents hydrogen or optionally methoxy-, ethoxy-, n- or i-propoxy-, acetyl-, propionyl, n- or i-butyroyl-, methoxycarbonyl-, ethoxycarbonyl-, n- or i-propoxycarbonyl-substituted methyl or ethyl, $R^4$ represents cyano, fluorine, chlorine, bromine, represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, $R^5$ represents cyano, fluorine, chlorine, bromine, represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, and $R^6$ represents hydrogen, represents cyano, fluorine, chlorine, bromine, represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy.

A very particularly preferred group are those compounds of the formula (I) in which A represents nitrogen or a CH grouping, E represents a single bond, Q represents oxygen or sulphur, $R^1$ represents hydrogen, fluorine, chlorine, bromine or in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^2$ represents fluorine, chlorine, bromine or in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^3$ represents hydrogen or optionally methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl or ethyl, $R^4$ represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, $R^5$ represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, and $R^6$ represents hydrogen, represents cyano, fluorine, chlorine, bromine, represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy.

Another very particularly preferred group are those compounds of the formula (I) in which A represents nitrogen or a CH grouping, E represents an NH grouping, Q represents oxygen or sulphur, R¹ represents hydrogen, fluorine, chlorine, bromine or in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, R² represents fluorine, chlorine, bromine or in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, R³ represents hydrogen or optionally methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl or ethyl, R⁴ represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, R⁵ represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, and R⁶ represents hydrogen, represents cyano, fluorine, chlorine, bromine, represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy.

The abovementioned general or preferred radical definitions apply both to the end products of the formula (I) and, correspondingly, to the starting materials or intermediates required in each case for the preparation. These radical definitions can be combined with each other as desired, that is to say combinations between the stated preferred ranges are also possible.

Using, for example, 2-amino-4-methoxy-6-methyl-pyrimidine and 2-ethyl-4-trifluoromethyl-thien-3-yl-sulphonyl isocyanate as starting materials, the course of the reaction in the process (a) according to the invention can be illustrated by the following equation:

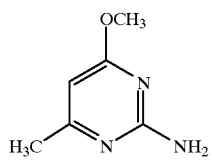

+

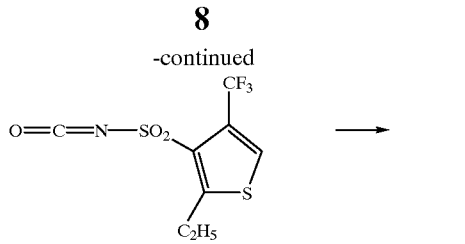

-continued

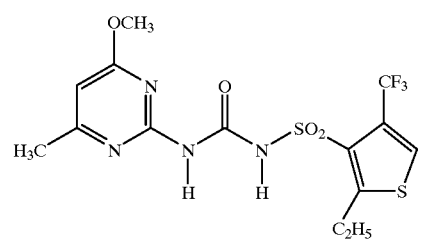

Using, for example, 2-methoxycarbonylamino-4-methoxy-6-trifluoromethyl-1,3,5-triazine and 4-ethyl-2-methyl-thiophene-3-sulphonamide as starting materials, the course of the reaction in the process (b) according to the invention can be illustrated by the following equation:

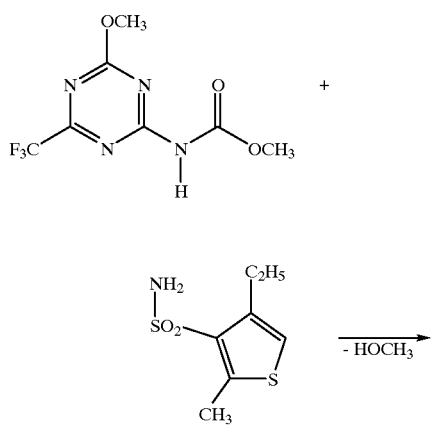

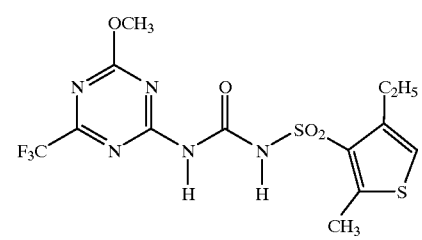

Using, for example, 2-amino-4-chloro-6-methoxy-pyrimidine and N-(2-chloro-4-methyl-thien-3-yl-sulphonyl)-O-phenyl-urethane as starting materials, the course of the reaction in the process (c) according to the invention can be illustrated by the following equation:

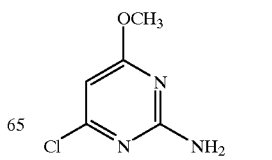

+

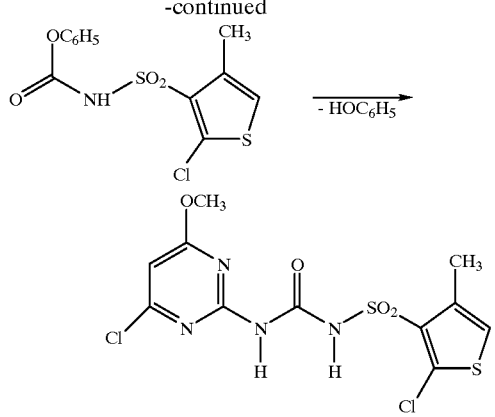

Using, for example, 2-amino-4-methoxy-6-methyl-1,3,5-triazine and chlorosulphonyl isocyanate and subsequently 3-amino-4-chloro-2-cyano-thiophene as starting materials, the course of the reaction in process (d) according to the invention can be illustrated by the following equation:

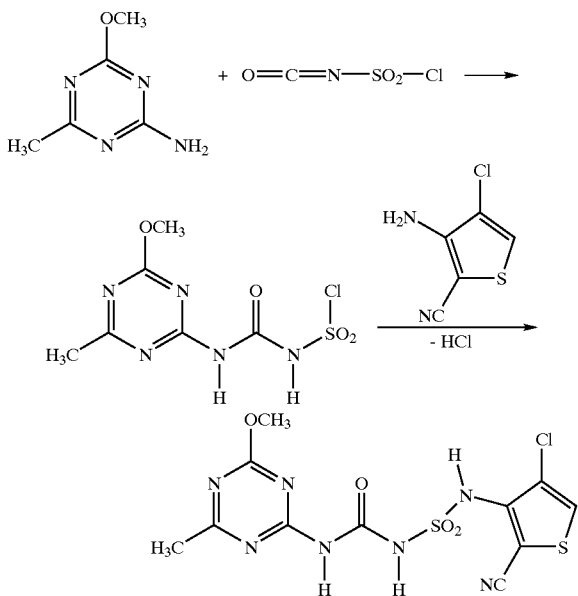

The formula (II) provides a general definition of the aminoazines to be used as starting materials in the process (a) (c) and (d) according to the invention for preparing the compounds of the general formula (I). In the formula (II), A, $R^1$, $R^2$ and $R^3$ each preferably or in particular have those meanings which have already been indicated above, in connection with the description of the compounds of the formula (I), as being preferred or particularly preferred for A, $R^1$, $R^2$ and $R^3$.

The aminoazines of the formula (II) are known chemicals for synthesis, some of which are commercially available.

The formula (III) provides a general definition of the thienylsulphonyl iso(thio)cyanates further to be used as starting materials in the process (a) according to the invention. In the formula (III), Q, $R^4$, $R^5$ and $R^6$ each preferably or in particular have those meanings which have already been indicated above, in connection with the description of the compounds of the formula (I), as being preferred or particularly preferred for Q, $R^4$, $R^5$ and $R^6$.

The starting materials of formula (III) are known and/or can be prepared by processes known per se (cf. EP 30142)

and are the subject-matter of a previous application not published before the date of the present application (cf. DE 19650196.2 of Apr. 12, 1996/"Le A 32 173").

The thienylsulphonyl iso(thio)cyanates of the formula (III) are obtained when thiophenesulphonamides of the general formula (V)—above—are reacted with phosgene or thiophosgene, if appropriate in the presence of an alkyl isocyanate, such as, for example, butyl isocyanate, if appropriate in the presence of a reaction auxiliary, such as, for example, diazabicyclo[2.2.2]octane, and in the presence of a diluent, such as, for example, toluene, xylene or chlorobenzene, at temperatures between 80° C. and 150° C., and the volatile components are distilled off under reduced pressure after the reaction has ended (cf. the Preparation Examples).

The formula (IV) provides a general definition of the substituted aminoazines to be used as starting materials in the process (b) according to the invention for preparing compounds of the formula (I). In the formula (IV), A, Q, $R^1$, $R^2$ and $R^3$ each preferably or in particular have those meanings which have already been indicated above, in connection with the description of the compounds of the formula (I), as being preferred or particularly preferred for A, Q, $R^1$, $R^2$ or $R^3$; Z preferably represents fluorine, chlorine, bromine, $C_1$–$C_4$-alkoxy or phenoxy, in particular chlorine, methoxy, ethoxy or phenoxy.

The starting materials of the formula (IV) are known and/or can be prepared by processes known per se (cf. U.S. Pat. No. 4,690,707, DE 19501174, Preparation Examples).

The formula (V) provides a general definition of the thiophenesulphonamides further to be used as starting materials in the process (b) according to the invention. In the formula (V), $R^4$, $R^5$ and $R^6$ each preferably or in particular have those meanings which have already been indicated above, in connection with the description of the compounds of the formula (I), as being preferred or particularly preferred for $R^4$, $R^5$ and $R^6$.

The starting materials of the formula (V) are known and/or can be prepared by processes known per se (cf. EP 30142).

The formula (VI) provides a general definition of the substituted thiophene-sulphon(thio)amides to be used as starting materials in the process (c) according to the invention for preparing the compounds of the formula (I). In the formula (VI), Q, $R^4$, $R^5$ and $R^6$ each preferably or in particular have those meanings which have already been indicated above, in connection with the description of the compounds of the formula (I), as being preferred or particularly preferred for Q, $R^4$, $R^5$ and $R^6$; Z preferably represents fluorine, chlorine, bromine, $C_1$–$C_4$-alkoxy or phenoxy, in particular chlorine, methoxy, ethoxy or phenoxy.

The starting materials of formula (VI) are known and/or can be prepared by processes known per se.

The formula (VIII) provides a general definition of the aminothiophenes to be used as starting materials in the process (d) according to the invention for preparing the compounds of the formula (I). In the formula (VIII), $R^4$, $R^5$ and $R^6$ each preferably or in particular have those meanings which have already been indicated above, in connection with the description of the compounds of the formula (I) according to the invention, as being preferred or particularly preferred for $R^4$, $R^5$ and $R^6$.

The starting materials of the formula (VIII) are known and/or can be prepared by processes known per se (cf. DE 3303388, U.S. Pat. No. 5,457,085).

Suitable diluents for carrying out the processes (a), (b), (c) and (d) according to the invention are, in particular, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate; sulphoxides, such as dimethyl sulphoxide.

The processes (a), (b), (c) and (d) according to the invention are preferably carried out in the presence of a suitable reaction auxiliary. Suitable reaction auxiliaries are all customary inorganic or organic bases. These include, for example, alkaline earth metal or alkali metal hydrides, hydroxides, amides, alkoxides, acetates, carbonates or dicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the processes (a), (b), (c) and (d) according to the invention, the reaction temperatures can be varied within a relatively wide range. In general, the reaction is carried out at temperatures between −20 C. and +150 C., preferably between 0 C. and +120 C.

The processes (a), (b), (c) and (d) according to the invention are generally carried out under atmospheric pressure. However, it is also possible to carry out the processes according to the invention under elevated or reduced pressure—in general between 0.1 bar and 10 bar.

In the practice of the processes (a), (b), (c) and (d) according to the invention, the starting materials are generally employed in approximately equimolar amounts. However, it is also possible to employ one of the components in a relatively large excess. The reaction is generally carried out in a suitable solvent in the presence of a reaction auxiliary, and the reaction mixture is generally stirred for a number of hours at the temperature required. Work-up is carried out by customary methods (cf. the Preparation Examples).

If required, salts of the compounds of the general formula (I) according to the invention can be prepared. Such salts are obtained in a simple manner by customary methods of forming salts, for example by dissolving or dispersing a compound of the formula (I) in a suitable solvent, such as, for example, methylene chloride, acetone, tert-butyl methyl ether or toluene, and addition of a suitable base. The salts can then be isolated—if required after prolonged stirring—by concentration or filtration with suction.

The active compounds according to the invention can be used as defoliants, desiccants, haulm killers and, especially, as weedkillers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, sports fields and pastureland and for the selective control of weeds in annual crops.

The compounds of the formula (I) according to the invention are suitable in particular for selectively controlling monocotyledonous and dicotyledonous weeds in monocotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to use for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, and natural phospholipids, such as cephalins and lecithins, and synthetic phospholipids, can be used in the formulations. Possible further additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachilor, butylate, cafenstrole, carbetamide, chlomethoxyfen, chloramben, chloridazon, chlorimuronl(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop(-ethyl), flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorocloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, menoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, plenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

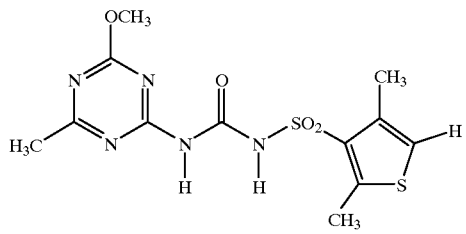

(Process (a))

At room temperature (approximately 20° C.), 1.7 g (7.8 mmol) of 2,4-dimethyl-thien-3-yl-sulphonyl isocyanate are added with stirring to a mixture of 1.01 g (7.8 mmol) of 2-amino-4-methoxy-6-methyl-1,3,5-triazine and 40 ml of acetonitrile. The reaction mixture is then heated under reflux for 12 hours and allowed to cool to room temperature. The resulting crystalline product is then isolated by filtration with suction.

This gives 2.08 g (75% of theory) of N-(4-methoxy-6-methyl-1,3,5-triazin-2-yl)-N'-(2,4-dimethyl-thien-3-yl-sulplhonyl)-urea of melting point 189° C.

Example 2

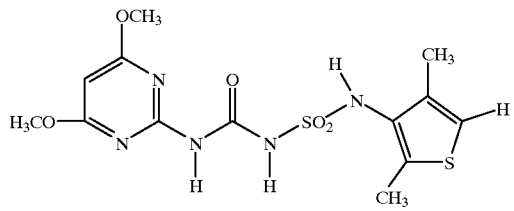

(Process (d))

2.78 g (19.7 mmol) of chlorosulphonyl isocyanate are dissolved in 200 ml of methylene chloride and cooled to −10° C. A solution of 3.05 g (19.7 mmol) of 2-amino-4,6-dimethoxy-pyrimidine in 50 ml of methylene chloride is then added dropwise with stirring, and the mixture is stirred at 0° C. for 30 minutes. A solution of 2.5 g (10.7 mmol) of 3-amino-2,4-dimethyl-thiophene and 2.0 g (20 mmol) of triethylamine in 100 ml of methylene chloride is subsequently added dropwise. The reaction mixture is then stirred at room temperature (approximately 20° C.) for 15 hours. 100 ml of 1N hydrochloric acid are subsequently added dropwise; the organic phase is separated off, washed with water, dried with magnesium sulphate and filtered. The filtrate is concentrated under water pump vacuum, the residue is digested with ethanol and the resulting crystalline product is isolated by filtration with suction.

This gives 4.4 g (58% of theory) of N-(4,6-dimethoxy-pyrimidin-2-yl)-N'-(2,4-dimethyl-thien-3-yl-aminosulphonyl)-urea of melting point 190° C.

Similarly to Preparation Examples 1 and 2 and in accordance with the general description of the preparation processes according to the invention, it is also possible to prepare, for example, the compounds of the formula (I) listed in Table 1 below.

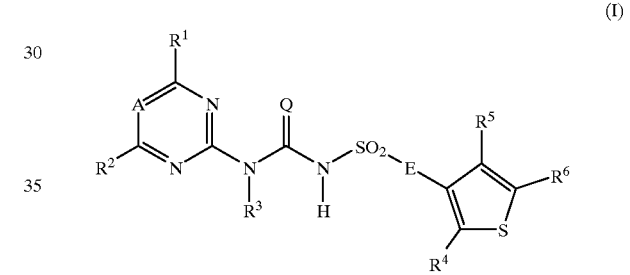

Table 1: Examples of compounds of the formula (I)

TABLE 1

Examples of compounds of the formula (I)

| Ex. No. | A | E | Q | R¹ | R² | R³ | R⁴ | R⁵ | R⁶ | Melting point (° C.) |
|---|---|---|---|---|---|---|---|---|---|---|
| 3 | N | NH | O | CH₃ | OCH₃ | H | CH₃ | CH₃ | H | 62 |
| 4 | N | NH | O | OCH₃ | OCH₃ | H | CH₃ | CH₃ | H | 170 |
| 5 | CH | NH | O | Cl | OCH₃ | H | CH₃ | CH₃ | H | 100 |
| 6 | N | — | O | OCH₂CF₃ | N(CH₃)₂ | H | CH₃ | CH₃ | H | 195 |
| 7 | CH | — | O | OCH₃ | OCH₃ | H | CH₃ | CH₃ | H | 198 |
| 8 | N | — | O | OC₆H₅ | N(CH₃)₂ | H | CH₃ | CH₃ | H | 173 |
| 9 | N | — | O | OCH₃ | OCH₃ | H | CH₃ | CH₃ | H | 168 |
| 10 | N | — | O | OCH₃ | cyclopropyl | H | CH₃ | CH₃ | H | 180 |
| 11 | N | — | O | CH₃ | SCH₃ | H | CH₃ | CH₃ | H | 220 |
| 12 | N | — | O | CH₃ | OC₂H₅ | H | CH₃ | CH₃ | H | 144 |
| 13 | N | — | O | C₂H₅ | OCH₃ | H | CH₃ | CH₃ | H | 161 |
| 14 | CH | — | O | CH₃ | CH₃ | H | CH₃ | CH₃ | H | 240 |
| 15 | CH | — | O | CH₃ | OCH₃ | H | CH₃ | CH₃ | H | 140 |
| 16 | CH | — | O | Cl | OCH₃ | H | CH₂ | CH₃ | H | 219 |

Starting Materials of the Formula (III)

Example (III-1)

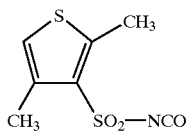

A mixture of 19.1 g (100 mmol) of 2,4-dimethyl-thiophene-3-sulplonamide, 10.0 g (100 mmol) of butylisocyanate and 100 ml of chloroform is heated to the boil, and at reflux temperature, phosgene is introduced into the mixture for 4 hours. The mixture is subsequently concentrated under water pump vacuum and the residue is subjected to a distillation under oil pump vacuum.

This gives 10.3 g (47% of theory) of 2,4-dimethyl-thien-3-yl-sulphonyl isocyanate having a boiling range of from 135° C. to 140° C. (at 1 mbar).

Starting Materials of the Formula (V)

Example (V-1)

Step 1

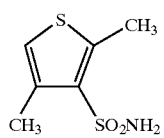

Step 1

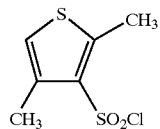

A solution of 13.9 g (109 mmol) of 3-amino-2,4-dimethyl-thiophene in 30 ml of 10% strength hydrochloric acid is cooled to 0° C. and admixed with 50 ml of conc. hydrochloric acid. With cooling to from 0° C. to −5° C., a solution of 8.6 g (125 mmol) of sodium nitrite in 22 ml of water is then added dropwise with stirring. The reaction mixture is stirred at from 0° C. to −5° C. for approximately one hour. Excess sodium nitrite is then destroyed with amidosulphonic acid. The resulting diazonium salt solution is then added dropwise at approximately 15° C. to a solution of 12 g of sulphur dioxide in 100 ml of 1,2-dichloro-ethane. 600 mg of copper(I) chloride and 600 mg of dodecyl-trimethlyammonium bromide are then added, and the reaction mixture is stirred for approximately one hour at approximately 40° C. and for a further 12 hours at room temperature (approximately 20° C.). After addition of 6 g of 30% strength hydrogen peroxide solution, the mixture is stirred for a further 30 minutes. The organic phase is then separated off, washed twice with water, dried with magnesium sulphate and filtered. The filtrate is concentrated under water pump vacuum, the residue is digested with petroleum ether and the resulting crystalline product is isolated by filtration with suction.

This gives 9.6 g (42% of theory) of 2,4-dimethyl-thiophene-3-sulphonyl chloride of melting point 79° C.

Step 2

Step 2

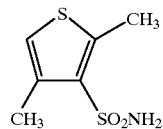

A mixture of 6.0 g (29 mmol) of 2,4-dimethyl-thiophene-3-sulphonyl chloride and 30 ml of 25% strength aqueous ammonia solution is stirred at room temperature (approximately 20° C.) for 12 hours. The resulting crystalline product is then isolated by filtration with suction.

This gives 4.3 g (80% of theory) of 2,4-dimethyl-thiophene-3-sulphonamide of melting point 135° C.

USE EXAMPLES

Example A

Pre-emergence-Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example the compounds of Preparation Example 1, 6, 7, 8, 9, 10, 12, 14, 15 and 16 exhibit very strong activity against weeds, and some of them are well tolerated by crop plants, such as, for example, wheat and barley (cf. Tables A-1 to A-10); "ai." active ingredient (active compound).

TABLE A-1

Pre-emergence Test/Greenhouse

| Active compound of Preparation Ex. No. | Application rate (g of ai./ha) | Barley | Wheat | Alopecurus | Lolium | Amaranthus | Chenopodium | Matricaria | Veronica |
|---|---|---|---|---|---|---|---|---|---|
| (1) | 4 | 0 | 0 | 100 | 100 | 100 | 100 | 100 | 100 |

TABLE A-2

Pre-emergence Test/Greenhouse

| Active compound of Preparation Ex. No. | Application rate (g of ai./ha) | Avena fatua | Amaranthus | Galium | Sinapis |
|---|---|---|---|---|---|
| (6) | 125 | 80 | 90 | 100 | 90 |

TABLE A-3
Pre-emergence Test/Greenhouse
| Active compound of Preparation Ex. No. | Application rate (g of ai./ha) | Wheat | Echino-chloa | Lolium | Cheno-podium | Matri-caria |
|---|---|---|---|---|---|---|
| 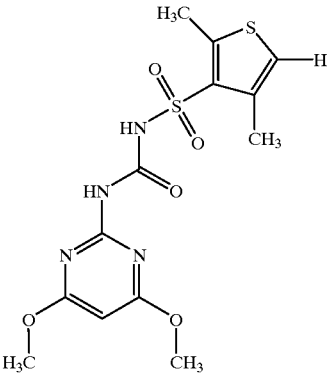<br>(7) | 60 | 10 | 95 | 95 | 90 | 95 |
TABLE A-4
Pre-emergence Test/Greenhouse
| Active compound of Preparation Ex. No. | Application rate (g of ai./ha) | Avena fatua | Amaran-thus | Galium | Sinapis |
|---|---|---|---|---|---|
| 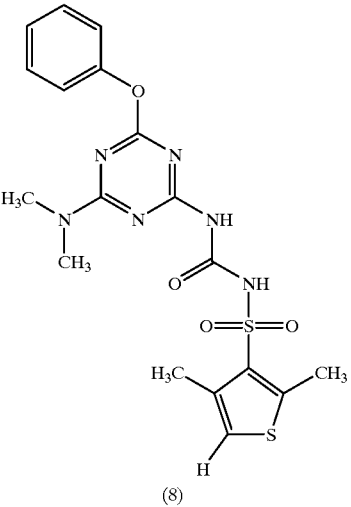<br>(8) | 125 | 80 | 80 | 90 | 80 |

TABLE A-5
Pre-emergence Test/Greenhouse
| Active compound of Preparation Ex. No. | Application rate (g of ai./ha) | Abutilon | Amaranthus | Sinapis |
|---|---|---|---|---|
| 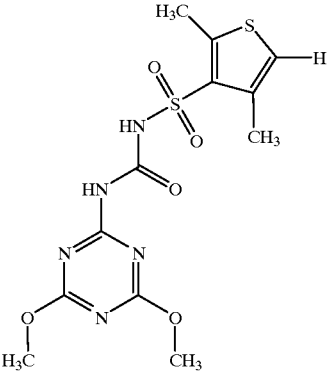 (9) | 60 | 90 | 90 | 90 |
TABLE A-6
Pre-emergence Test/Greenhouse
| Active compound of Preparation Ex. No. | Application rate (g of ai./ha) | Setaria | Amaranthus | Galium |
|---|---|---|---|---|
| 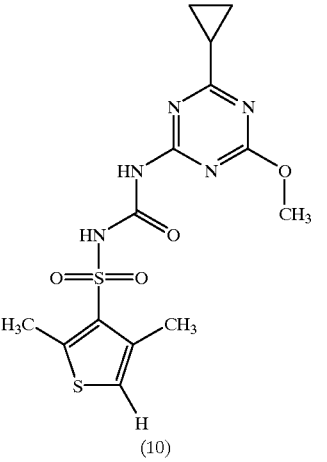 (10) | 60 | 80 | 80 | 100 |

TABLE A-7
Pre-emergence Test/Greenhouse
| Active compound of Preparation Ex. No. | Application rate (g of ai./ha) | Alope-curus | Abuti-lon | Ama-ranthus | Sinapis |
|---|---|---|---|---|---|
| 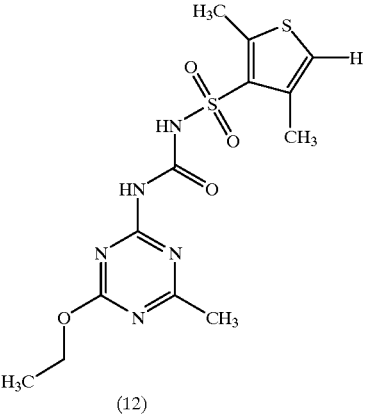 (12) | 60 | 80 | 90 | 90 | 90 |
TABLE A-8
Pre-emergence Test/Greenhouse
| Active compound of Preparation Ex. No. | Application rate (g of ai./ha) | Cyperus | Amaran-thus | Sinapis |
|---|---|---|---|---|
| 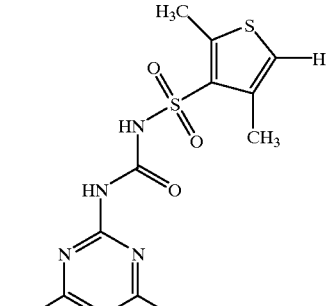 (14) | 60 | 100 | 90 | 90 |

TABLE A-9

Pre-emergence Test/Greenhouse

| Active compound of Preparation Ex. No. | Application rate (g of ai./ha) | Abutilon | Amaranthus | Sinapis |
|---|---|---|---|---|
| (15) [structure] | 60 | 100 | 90 | 100 |

TABLE A-10

Pre-emergence Test/Greenhouse

| Active compound of Preparation Ex. No. | Application rate (g of ai./ha) | Cyperus | Amaranthus | Sinapis |
|---|---|---|---|---|
| (16) [structure] | 60 | 80 | 95 | 95 |

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example the compounds of Preparation Example 1, 6, 7, 9, 11, 12, 13, 14, 15 and 16 exhibit strong activity against weeds (cf. Tables B-1 to B-10).

TABLE B-1
Post-emergence Test/Greenhouse
| Active compound of Preparation Ex. No. | Application rate (g of ai./ha) | Abutilon | Amaranthus | Chenopodium | Matricaria | Xanthium |
|---|---|---|---|---|---|---|
| 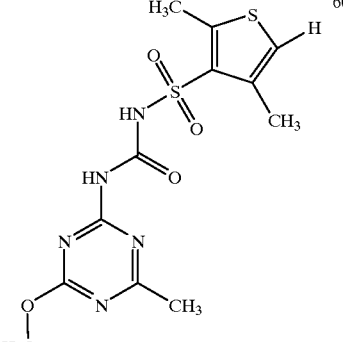 (1) | 60 | 95 | 95 | 100 | 95 | 100 |
TABLE B-2
Post-emergence Test/Greenhouse
| Active compound of Preparation Ex. No. | Application rate (g of ai./ha) | Alopecurus | Amaranthus | Sinapis |
|---|---|---|---|---|
| 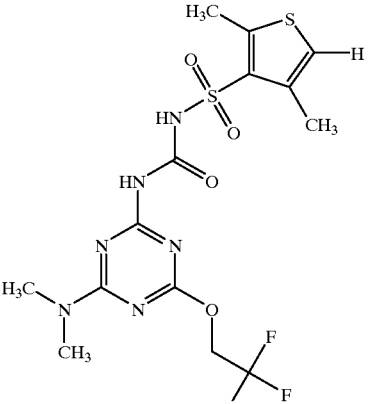 (6) | 125 | 100 | 80 | 100 |

TABLE B-3

Post-emergence Test/Greenhouse

| Active compound of Preparation Ex. No. | Application rate (g of ai./ha) | Abutilon | Amaranthus | Chenopodium | Matricaria | Xanthium |
|---|---|---|---|---|---|---|
| (7) | 60 | 95 | 95 | 95 | 95 | 95 |

TABLE B-4

Post-emergence Test/Greenhouse

| Active compound of Preparation Ex. No. | Application rate (g of ai./ha) | Abutilon | Amaranthus | Sinapis |
|---|---|---|---|---|
| (9) | 60 | 80 | 100 | 95 |

TABLE B-5

Post-emergence Test/Greenhouse

| Active compound of Preparation Ex. No. | Application rate (g of ai./ha) | Amaranthus | Sinapis |
|---|---|---|---|
| (11) | 60 | 100 | 100 |

TABLE B-6

Post-emergence Test/Greenhouse

| Active compound of Preparation Ex. No. | Application rate (g of ai./ha) | Alopecurus | Abutilon | Amaranthus | Sinapis |
|---|---|---|---|---|---|
| (12) | 60 | 80 | 90 | 100 | 100 |

TABLE B-7

Post-emergence Test/Greenhouse

| Active compound of Preparation Ex. No. | Application rate (g of ai./ha) | Abutilon | Amaranthus | Sinapis |
|---|---|---|---|---|
| (13) | 60 | 90 | 100 | 95 |

TABLE B-8

Post-emergence Test/Greenhouse

| Active compound of Preparation Ex. No. | Application rate (g of ai./ha) | Alopecurus | Amaranthus | Sinapis |
|---|---|---|---|---|
| (14) | 60 | 80 | 100 | 100 |

TABLE B-9

Post-emergence Test/Greenhouse

| Active compound of Preparation Ex. No. | Application rate (g of ai./ha) | Setaria | Abutilon | Amaranthus | Sinapis |
|---|---|---|---|---|---|
| 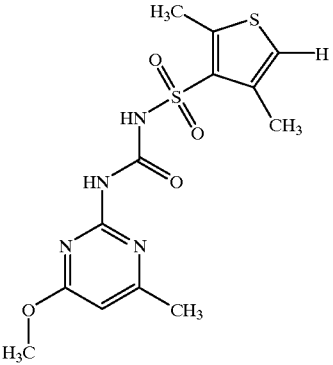 (15) | 60 | 90 | 90 | 100 | 100 |

TABLE B-10

Post-emergence Test/Greenhouse

| Active compound of Preparation Ex. No. | Application rate (g of ai./ha) | Amaranthus | Sinapis |
|---|---|---|---|
| 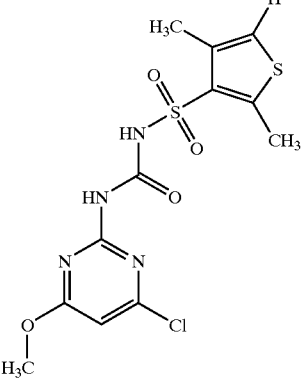 (16) | 60 | 100 | 95 |

What is claimed is:

1. A substituted thienyl(amino)sulphonyl(thio)urea of the formula (I)

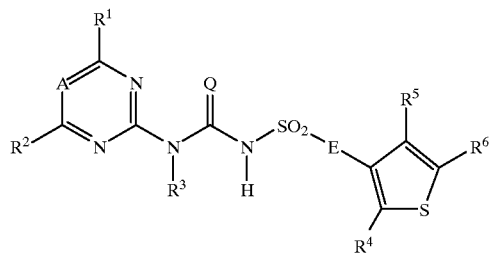

wherein

A represents a CH grouping,

E represents a single bond or an NH grouping,

Q represents oxygen or sulphur, $R^1$ represents a member selected from the group consisting of hydrogen; halogen; unsubstituted or cyano-, halogen- or, $C_1$–$C_4$-alkoxy-substituted alkyl, alkoxy, alkylthio, alkyamino or dialkylamino having in each case 1 to 4 carbon atoms in the alkyl groups; unsubstituted or cyano-, halogen-, $C_1$–$C_4$-alkyl- or $C_1$–$C_4$-alkoxy-substituted cycloalkyl or cycloalkyloxy having in each case 3 to 6 carbon atoms; and unsubstituted or cyano-, halogen-, $C_1$–$C_4$-alkyl- or $C_1$–$C_4$-alkoxy-substituted phenoxy, oxetanyloxy, furyloxy or tetrahydrofuryloxy;

$R^2$ represents a member selected from the group consisting of hydrogen; or halogen; unsubstituted or cyano-, halogen- or $C_1$–$C_4$-alkoxy-substituted alkyl, alkoxy, alkylthio, alkylamino or dialyklamino having in each case 1 to 4 carbon atoms in the alkyl groups; unsubstituted or cyano-, halogen-, $C_1$–$C_4$-alkyl- or $C_1$–$C_4$- alkoxy-substituted cycloalkyl or cycloalkyloxy having in each case 3 to 6 carbon atoms; and unsubstituted or cyano-, halogen-, $C_1$–$C_4$-alkyl- or $C_1$–$C_4$-alkoxy- substituted phenoxy, oxetanyloxy, furloxy or tetrahydroxyfuryloxy;

$R^3$ represents a member selected from the group consisting of hydrogen, unsubstituted alkyl having 1 to 4 carbon atoms and $C_1$–$C_4$-alkoxy-, $C_1$–$C_4$-alkyl-carbonyl- or $C_1$–$C_4$-alkoxy-carbonyl-substituted alkyl having 1 to 4 carbon atoms, $R^4$ represents a member selected from the group consisting of halogen; unsubstituted or $C_1$–$C_4$-alkoxy-substituted $C_{1-C4}$-alkyl; unsubstituted or cyano- or halogen-substituted $C_2$–$C_4$-alkenyl or $C_2$–$C_4$-alkinyl; unsubstituted or cyano-, halogen- or $C_{1-C4}$-alkoxy-substituted $C_1$–$C_4$-alkoxy; and unsubstituted or cyano- or halogen-substituted $C_2$–$C_4$-alkenyloxy or $C_2$–$C_4$-alkinyloxy;

$R^5$ represents a member selected from the group consisting of halogen; unsubstituted or $C_1$–$C_4$-alkoxy-unsubstituted $C_1$–$C_4$-alkyl; unsubstituted or cyano- or halogen-substituted $C_2$–$C_4$-alkenyl or $C_2$–$C_4$-alkinyl; unsubstituted or cyano-, halogen- or $C_1$–$C_4$-alkoxy-substituted $C_1$–$C_4$-alkoxy; and unsubstituted or cyano- or halogen-substituted $C_2$–$C_4$-alkenyloxy or $C_2$–$C_4$-alkinyloxy; and $R^6$ represents a member selected from the group consisting of hydrogen; halogen; unsubstituted or cyano-, halogen-, $C_1$–$C_4$-alkoxy-substituted $C_1$–$C_4$-alkyl; unsubstituted or cyano- or halogen-substituted $C_2$–$C_4$-alkenyl or $C_2$–$C_4$-alkinyl; unsubstituted or cyano-, halogen- or $C_1$–$C_4$-alkoxy-substituted $C_1$–$C_4$-alkoxy; and unsubstituted or cyano- or halogen-substituted $C_2$–$C_4$-alkenyloxy or $C_2$–$C_4$-alkinyloxy; and/or a salt of the compound of the formula (I).

2. The compound of claim 1, wherein the compound is a salt, said salt being selected from the group consisting of the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of said compound.

3. The compound of claim 1, wherein

A represents a CH grouping,

E represents a single bond or an NH grouping,

Q represents oxygen or sulphur, $R^1$ represents a member selected from the group consisting of hydrogen; flourine; chlorine; bromine; unsubstituted or cyano-, fluorine-, chlorine-, methoxy or ethoxy- substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino and diethylamino;

$R^2$ represents a member selected from the group consisting of hydrogen; flourine; chlorine; bromine; unsubstituted or cyano-, fluorine-, chlorine-, methoxy or ethoxy-substituted methyl, ethyl, n- or i-propyl, methoxy, ethoxy, n- or i-propoxy, methylthio, ethylthio, n- or i-propylthio, methylaminom ethylamino, n- or i-propylamino, dimethylamino and diethylamino;

$R^3$ represents a member selected from the group consisting of hydrogen; methyl; ethyl; and methoxy-, ethoxy-, n- or i-propoxy-, acetyl-, propionyl-, n- or i-butroyl-, methoxycarbonyl, ethoxycarbonyl-, n- or i-propoxycarbonyl-substituted methyl or ethyl;

$R^4$ represents a member selected from the group consisting of fluorine; chlorine; bromine; unsubstituted or methoxy- or ethoxy-substituted methyl, ethyl, n- or i-propyl, n-, i-, or s-butyl-; unsubstituted or cyano-, fluorine- or chlorine-substituted propenyl, butenyl, propinyl or butinyl; unsubstituted or cyano-, fluorine-, chlorine-, methoxy- or ethoxy- substituted methoxy, ethoxy, n- or i-propoxy, n-, i-, s- or t-butoxy; and unsubstituted or cyano-, fluorine- or chlorine-substituted propenyloxy, butenyloxy, propinyloxy or butinloxy;

$R^5$ represents a member selected from the group consisting of fluorine; chlorine; bromine; unsubstituted or methoxy- or ethoxy-substituted methyl, ethyl, n- or i-propyl, n-, i-, or s-butyl-; unsubstituted or cyano-, fluorine- or chlorine-substituted propenyl, butenyl, propinyl or butinyl; unsubstituted or cyano-, fluorine-, chlorine-, methoxy-, or ethoxy- substituted methoxy, ethoxy, n- or i-propoxy, n-, i-, s- or t-butoxy; and unsubstituted or cyano-, fluorine- or chlorine-substituted propenyloxy, butenyloxy, propinyloxy or butinyloxy; and $R^6$ represents a member selected from the group consisting of hydrogen; fluorine; chlorine; bromine; unsubstituted or cyano-, fluorine-, chlorine-, methoxy- or ethoxy-substituted methyl, ethyl, n- or i-propyl, n-, i-, or s- butyl-; unsubstituted or cyano-, fluorine- or chlorine-substituted propenyl, butenyl, propinyl or butinyl; unsubstituted or cyano-, fluorine-, chlorine-, methoxy- or ethoxy-substituted methoxy, ethoxy, n- or i- propoxy, n-, i-, s- or t-butoxy; and unsubstituted or cyano-, fluorine- or chlorine-substituted propenyloxy, butenyloxy, propinyloxy or butinloxy.

4. A herbicidal composition comprising one or more compounds of the formula (I) or one of its salts according to claim 1 and an inert carrier.

5. A method for controlling weeds, comprising the step of applying an effective amount of one or more compounds of the formula (I) or salts thereof according to claim 1 on the weeds or their habitat.

6. A method for controlling undesirable plant growth comprising the step of applying an effective amount of one or more compounds of the formula (I) or salts thereof according to claim 1 to the undesirable plant growth or their habitat.

7. The compound of claim 3 wherein

E represents a single bond, $R^4$ represents a member selected from the group consisting of unsubstituted or methoxy- or ethoxy-substituted methyl, ethyl, n- or i-propyl, n-, i-, or s-butyl-; unsubstituted or cyano-, fluorine- or chlorine-substituted propenyl, butenyl, propinyl or butinyl; unsubstituted or cyano-, fluorine-, chlorine-, methoxy- or ethoxy- substituted methoxy, ethoxy, n- or i-propoxy, n-, i-, s- or t-butoxy; and unsubstitited or cyano-, fluorine- or chlorine- substituted propenyloxy, butenloyxy, propinyloxy or butinloxy; and $R^5$ represents a member selected from the group consisting of unsubstituted or methoxy- or ethoxy-substituted methyl, ethyl, n- or i-propyl, n-, i-, or s-butyl-; unsubstituted or cyano-, fluorine- or chlorine-substituted propenyl, butenyl, propinyl or butinyl; unsubstituted or cyano-, fluorine-, chlorine-, methoxy- or ethoxy- substituted methoxy, ethoxy, n- or i-propoxy, n-, i- s-, or t-butoxy; and unsubstituted or cyano-, fluorine- or chlorine- substituted propenloxy, butenloxy, propinyloxy or butinyloxy.

8. The compound of claim 3 wherein

E represents an NH grouping, $R^4$ represents a member selected from the group consisting of unsubstituted or methoxy- or ethoxy-substituted methyl, ethyl, n- or i-propyl, n-, i-, or s-butyl-; unsubstituted or cyano-, fluorine- or chlorine-substituted propenyl, butenyl, propinyl or butinyl; unsubstituted or cyano-, fluorine-, chlorine-, methoxy- or ethoxy- substituted methoxy, ethoxy, n- or i-propoxy, n-, i-, s- or t-butoxy; and unsubstantiated or cyano-, fluorine- or chlorine- substituted propenyloxy, butenloxy, propinyloxy or butinloxy; and $R^5$ represents a member selected from the group consisting of unsubstituted or methoxy- or ethoxy-substituted methyl, ethyl, n- or i-propyl, n-, i-, or s-butyl-; unsubstituted or cyano-, fluorine- or chlorine-substituted propenyl, butenyl, propinyl or butinyl; unsubstituted or cyano-, fluorine-, chlorine-, methoxy- or ethoxy-substituted methoxy, ethoxy, n- or i-propoxy, n-, i- s-, or t-butoxy; and unsubstituted or cyano-, fluorine- or chlorine-substituted propenloxy, butenloxy, propinyloxy or butinyloxy.

9. A substituted thienyl(amino)sulphony(thio)urea according to claim 1, wherein at least two of $R^4$, $R^5$, and $R^6$ are unsubstituted $C_1$–$C_4$-alkyls.

10. A substitued thienyl(amino)sulphony(thio)urea according to claim 1, wherein $R^4$ and $R^5$ each represent an unsubstituted $C_1$ to $C_4$-alkyl and $R^6$ represents hydrogen.

* * * * *